US009119611B2

United States Patent
Super et al.

(10) Patent No.: US 9,119,611 B2
(45) Date of Patent: Sep. 1, 2015

(54) CORNER PROTECTOR FOR INSTRUMENT STERILIZATION TRAY

(71) Applicant: Summit Medical, Inc., St. Paul, MN (US)

(72) Inventors: Marcus Felipe Super, Minneapolis, MN (US); Daniel Broberg, Minnetonka, MN (US); Kevin D. McIntosh, Brooklyn Park, MN (US)

(73) Assignee: Summit Medical, Inc., St. Paul, MN (US)

( * ) Notice: Subject to any disclaimer, the term of this patent is extended or adjusted under 35 U.S.C. 154(b) by 0 days.

(21) Appl. No.: 14/336,534

(22) Filed: Jul. 21, 2014

(65) Prior Publication Data
US 2015/0021340 A1    Jan. 22, 2015

Related U.S. Application Data

(60) Provisional application No. 61/856,252, filed on Jul. 19, 2013.

(51) Int. Cl.
| | |
|---|---|
| *A47B 95/00* | (2006.01) |
| *A61B 19/02* | (2006.01) |
| *A61L 2/26* | (2006.01) |
| *A61B 19/00* | (2006.01) |

(52) U.S. Cl.
CPC ........... *A61B 19/0271* (2013.01); *A61B 19/026* (2013.01); *A61L 2/26* (2013.01); *A61B 2019/48* (2013.01)

(58) Field of Classification Search
CPC .......................... A61B 19/0271; A61B 19/026
USPC ................................................. 206/453, 586
See application file for complete search history.

(56) References Cited

U.S. PATENT DOCUMENTS

| | | | |
|---|---|---|---|
| 7,413,157 B2 | 8/2008 | Curnow et al. | |
| D602,350 S | 10/2009 | Lavelle | |
| 2009/0266739 A1* | 10/2009 | Kindig | 206/586 |
| 2011/0278199 A1* | 11/2011 | Dane et al. | 206/586 |

FOREIGN PATENT DOCUMENTS

| | | |
|---|---|---|
| EP | 0720569 B1 | 5/1997 |
| EP | 1051981 A1 | 11/2000 |

(Continued)

OTHER PUBLICATIONS

International Search Report and Written Opinion dated Oct. 23, 2014 for corresponding International Application No. PCT/US2014/047440, filed Jul. 21, 2014.

*Primary Examiner* — Steven A. Reynolds
*Assistant Examiner* — King M Chu
(74) *Attorney, Agent, or Firm* — Peter J. Ims; Westman, Champlin & Koehler, P.A.

(57) ABSTRACT

A corner protector for position about a corner of an equipment sterilization tray includes a base portion having a perimeter and a first concave recess. A first wall portion extends from a first portion of the perimeter of the base portion and comprises a second concave recess. A second wall portion extends from a second portion of the perimeter and comprises a third concave recess wherein the first and second wall portions are substantially perpendicular to each other. A connecting portion extends from a third portion of the perimeter wherein the connecting portion connects the first and second wall portions to form a continuous wall.

23 Claims, 10 Drawing Sheets

(56) References Cited

FOREIGN PATENT DOCUMENTS

| WO | 2007019233 | A3 | 2/2007 |
|----|------------|----|--------|
| WO | 2008094850 | A1 | 8/2008 |
| WO | 2011142939 | A3 | 11/2011 |
| WO | 2013039493 | A1 | 3/2013 |

* cited by examiner

CORNER PROTECTOR FOR INSTRUMENT STERILIZATION TRAY

CROSS REFERENCE TO RELATED APPLICATION(S)

The present application claims the benefit of U.S. Provisional Patent Application Ser. No. 61/856,252 entitled CORNER PROTECTOR FOR INSTRUMENT STERILIZATION TRAY, the contents of which are incorporated by reference in its entirety.

BACKGROUND

The discussion below is merely provided for general background information and is not intended to be used as an aid in determining the scope of the claimed subject matter.

The present disclosure relates to a corner protector for an instrument sterilization tray. More particularly, the present disclosure relates to a corner protector for an instrument sterilization tray that increases radii of edges defining a corner of the instrument sterilization tray.

Equipment sterilization trays are typically utilized to retain surgical instruments through the sterilization process. However, the trays themselves do not maintain a sterile barrier once they exit the autoclave. An uncompromised sterile barrier is of critical importance for hospitals and surgery centers in their fight against infection.

In order to maintain the sterility of the instruments after the sterilization process, a sterile barrier is typically utilized to ensure the sterility of the instruments. One way to maintain a sterile barrier is to utilize a separate sterile container to contain not only the instrument sterilization tray but also the instruments within the instrument sterilization tray.

An alternative to the separate sterile container is to utilize a sterile wrap. A sterile wrap is typically a fabric like material that completely covers or encases the instrument sterilization tray to provide a sterile barrier. The sterile wrap is utilized much in the same way that a paper is used to wrap a present, in that both completely encase an outer surface of the instrument sterilization tray or present.

Because the wrap maintains the sterility of the instruments within the equipment tray, it is important that the wrap is not torn subsequent to being sterilized. If the wrap is torn or punctured after the instruments have being sterilized, the torn wrap must be removed and the tray must be rewrapped and the sterilization process must be performed again.

The most common place where the wrap tears or is punctured is proximate the corner of the instrument sterilization trays. The instrument sterilization trays can have a somewhat sharp corner, and when pressure is improperly applied to the wrap, the corner can tend to tear through or puncture the wrap, and therefore break the sterile barrier.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the Background.

In one aspect the present disclosure relates to a combination foot and corner protector configured for use on a corner of an instrument sterilization tray. The foot and corner protector includes a flexible main body that encases a threaded metal insert having a threaded through bore. The threaded insert is positioned within a foot portion of the main body. A first wall portion extends upwardly from a first portion of a perimeter of the foot portion and a second wall portion extends upwardly from a second portion of the perimeter of the foot portion where the first and second side wall portions are substantially orthogonal to each other. An intermediate portion extends upwardly proximate a corner of the foot portion where the intermediate portion connects the first and second side wall portions to form a continuous side wall. A top surface of the foot portion, an inner surface of the first sidewall portion, an inner surface of the second wall portion and an inner surface of the middle corner portion are configured to conform to a portion of a foot and outer corner surfaces of a sterilization tray. The outer bottom surface of the foot portion, the outer side surface of the first side wall portion and the outer side surface of the second side wall portion are substantially flat and smooth. Outer surfaces of the intermediate portion and transitions between the outer bottom surface and the first and second side wall portions are rounded such that there are gradual and smooth transitions in the exterior surfaces between the portions of the main body. The foot and corner protector has no abrupt changes in the configuration of the exterior surface. Therefore, the corner is configured to protect a sterile wrap from tearing or being punctured when placed around an instrument sterilization tray. The foot and corner protector is removably secured to the instrument sterilization tray by inserting a bolt through an aperture in the bottom the sterilization tray and threadably engaging the threaded bore within the threaded insert.

In another aspect, the present disclosure relates to a corner protector configured for use on an instrument sterilization tray. The corner protector is a monolithic structure that includes a substantially continuous inner surface and a substantially continuous outer surface. The substantially continuous inner surface is defined by an inner surface of a base portion and inner surfaces of first and second wall portions extending from a perimeter of the base portion where the first and second wall portions are substantially orthogonal to each other. The corner protector includes first and second transition portions that connect the base portion to the first and second wall portions, respectively, and a third transition portion that connects the first and second wall portions and the base portion. The first, second and third transition portions are configured to engage the three edges of the instrument sterilization tray that defines the corner. The substantially continuous outer wall is defined by outer surfaces of the base portion, the first wall portion, the second wall portion and the first, second and third transition portions. The substantially continuous outer wall includes smooth, rounded transitions between the base and the first and second side portions and between the first and second side portions such there are no abrupt or sharp edges that could potentially tear or puncture a sterile wrap.

In another aspect, the present disclosure relates to a corner protector configured for use on an instrument sterilization tray. The corner protector is a monolithic structure that includes a substantially continuous inner surface and a substantially continuous outer surface where the substantially continuous inner and outer surfaces are defined by a base portion and first and second wall portions extending from the base portion where the first wall portion, the second wall portion and the base portion are connected together with transition portions that are configured to engage the three edges of the instrument sterilization tray that define a corner and outer radii to smoothly transition between the first wall portion, the second wall portion and the base portion to prevent the tearing or puncturing of a sterile wrap when placed about the instrument sterilization tray. The base portion, the first side wall portion and the second side wall portion includes concave areas on the inner surfaces and corresponding convex areas on the outer surface such that the concave portions are configured to be a distance from the walls of the instrument tray when positioned about the corner of the instrument sterilization tray. The convex areas of the base portion, the first side wall portion and the second side wall portion are configured to be movable toward the surfaces of the tray when a force is placed thereon to dissipate the force and further protect a sterile wrap when placed around the instrument sterilization tray.

In another aspect, the present disclosure relates to a corner protector configured for use on an instrument sterilization tray. The corner protector is a monolithic structure that includes a substantially continuous inner surface and a substantially continuous outer surface where the substantially continuous inner and outer surfaces are defined by a base portion and first and second wall portions extending from the base portion where the first wall portion, the second wall portion and the base portion are connected together with transition portions that are configured to engage the three edges of the instrument sterilization tray that define a corner and outer radii to smoothly transition between the first wall portion, the second wall portion and the base portion to prevent the tearing or puncturing of a sterile wrap when placed about the instrument sterilization tray. The corner protector includes a plurality of apertures therein wherein the plurality of apertures are substantially parallel and interrupt the interior and exterior surfaces of the first wall portion, the second wall portion and the base portion.

In another aspect, the present disclosure relates to a corner protector configured for use on an instrument sterilization tray. The corner protector is a monolithic structure that includes a substantially continuous inner surface and a substantially continuous outer surface where the substantially continuous inner and outer surfaces are defined by a base portion and first and second wall portions extending from the base portion where the first wall portion, the second wall portion and the base portion are connected together with transition portions that are configured to engage the three edges of the instrument sterilization tray that define a corner and outer radii to smoothly transition between the first wall portion, the second wall portion and the base portion to prevent the tearing or puncturing of a sterile wrap when placed about the instrument sterilization tray. A length and a mass of the base portion are sufficiently greater than a mass of the first and second wall portions such that a center of gravity of the corner protector is located in the base portion and at a selected distance from both the first and second wall portions such that corner protector is retained on an upper corner of the instrument sterilization tray when positioned thereon.

In all cases, this disclosure presents the disclosed subject matter by way of representation and not limitation. It should be understood that numerous other modifications and embodiments can be devised by those skilled in the art which fall within the scope and spirit of the principles of this disclosure.

The figures may not be drawn to scale. In particular, some features may be enlarged relative to other features for clarity. Moreover, where terms such as above, below, over, under, top, bottom, side, right, left, etc., are used, it is to be understood that they are used only for ease of understanding the description. It is contemplated that structures may be oriented otherwise.

DETAILED DESCRIPTION

Figure 1:
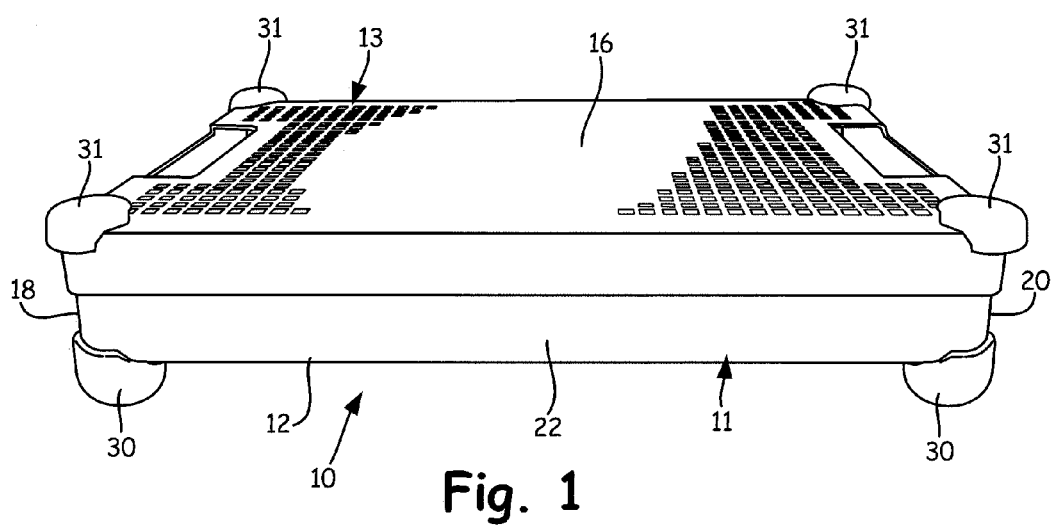
FIG. 1 is a perspective view of a sterilization tray with a cover having corner protectors positioned about all of the corners.

An equipment sterilization tray having foot and corner protectors is generally illustrated in FIG. 1 at 10. The equipment sterilization tray 10 typically includes a box portion 11 defined by a bottom surface 12, a left side wall 18 extending upwardly from a left side edge of the bottom surface 12, a right side wall 20 extending from an opposing edge, a front wall 22 and a back wall (not shown) extending from opposing front and back edges of the bottom surface 12. The equipment sterilization tray 10 includes a cover 13 having four walls 14 extending from a perimeter 15 of a top surface 16 where the four walls 14 extend over top portions of the four side walls 18, 20, 22 and (not shown) to retain the cover 13 to the box portion 11.

The box portion 11 defined by the four side walls 18, 20, 22 and (not shown) along with the bottom surface 12 defines a volume therein into which surgical instruments can be placed for sterilization. While not illustrated, it is contemplated to attach surgical instrument retaining devices to the bottom surface 12 that are configured to secure the position of instruments within the tray 10 prior to sterilization of the tray 10 and the enclosed instruments.

The box portion 11 and the cover 13 are typically made up of a metal, such as stainless steel. Because the box portion 11 is made of metal, the corners which are defined by the bottom surface 12 and two adjacent side walls, 18, 20, 22 and (not shown) tend to have sharp edges which can lead to a sterile wrap to tear through or puncture a sterile barrier which requires a re-sterilization process which is time consuming and costly. Utilizing a foot and corner protector 30 of the present disclosure on the all of corners prevents and/or tends to eliminate the issue of the corner of the sterilization tray 10 tearing through the sterile wrap.

The cover 13 also has four additional sharp corners. It is contemplated to utilize a corner protector 31 having a similar construction to the corner protectors 30 to cover the corners of the cover 13, where the corner protector 31 has shorter side walls than the corner protector 30. The corner protectors 31 can be attached to the four corners of the cover 13 with a threaded engagement with an insert similar to that disclosed with respect to the corner protector 30. It is also contemplated that other securing mechanisms besides a threaded engagement be used to secure the corner protectors 31 to the corners of the cover 13, such as but not limited gravity.

Figure 2:
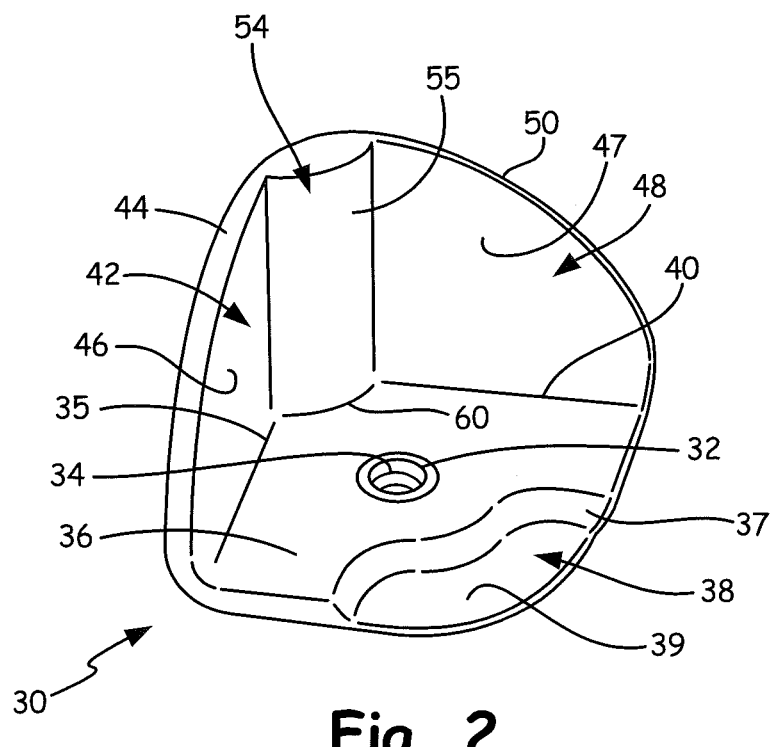
FIG. 2 is a perspective view of a sterilization tray having the foot and corner protectors attached thereto.
Figure 3:
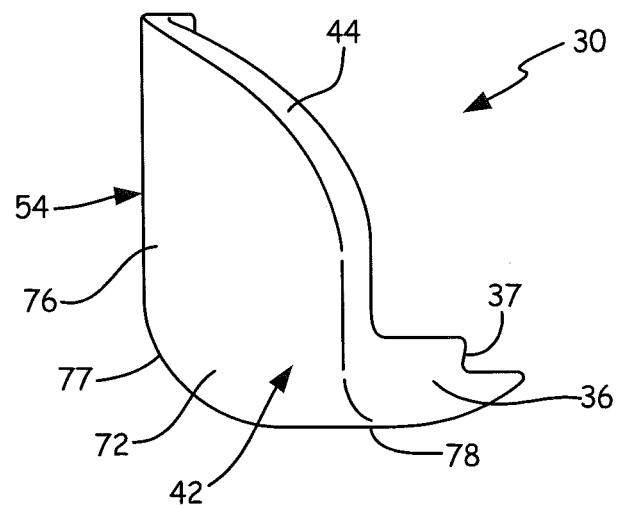
FIG. 3 is a left side view of the foot and corner protector.
Figure 4:
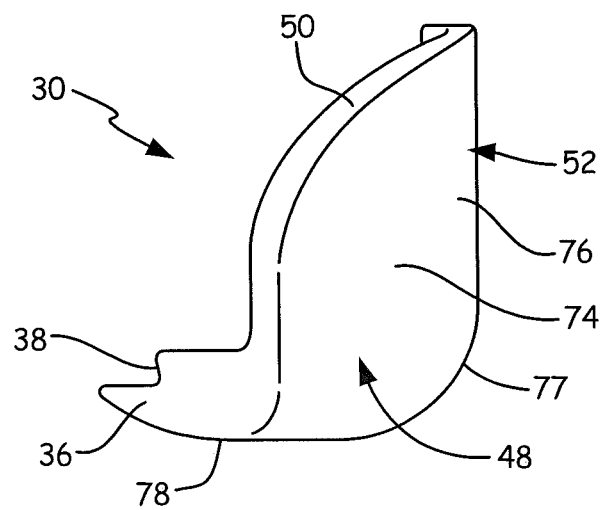
FIG. 4 is a right side view of the foot and corner protector.
Figure 5:
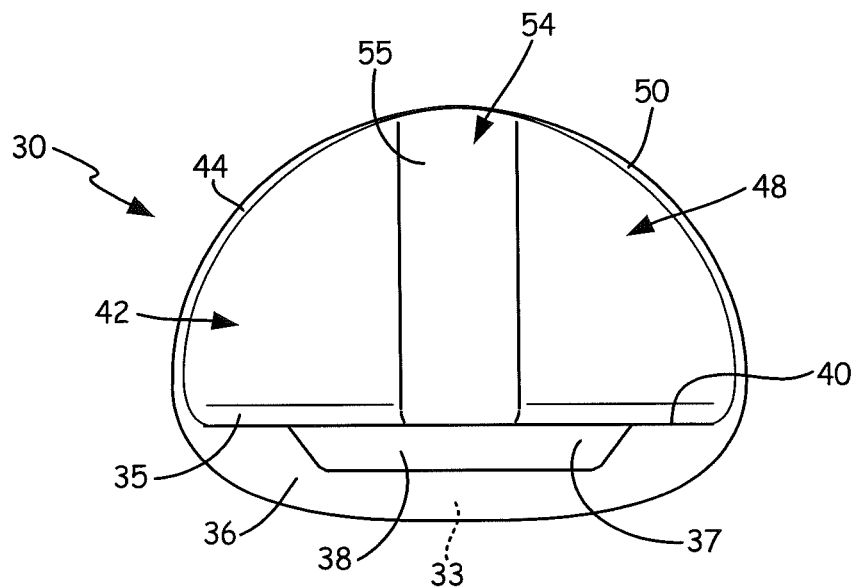
FIG. 5 is a front view of the foot and corner protector.
Figure 7:
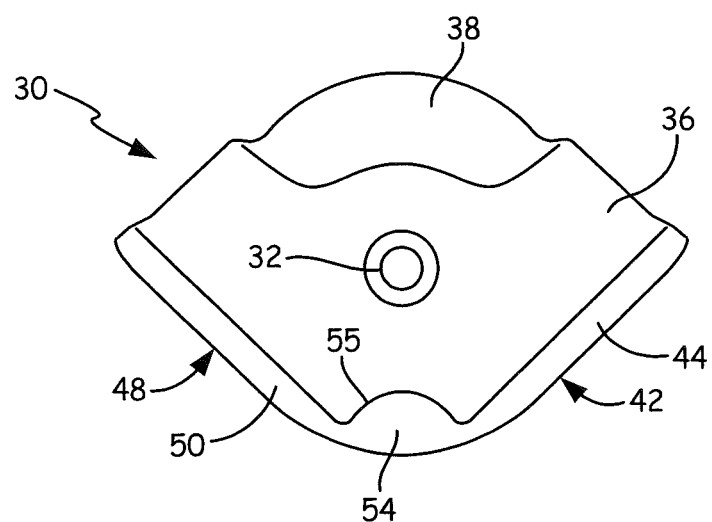
FIG. 7 is a top view of the foot and corner protector.
Figure 8:
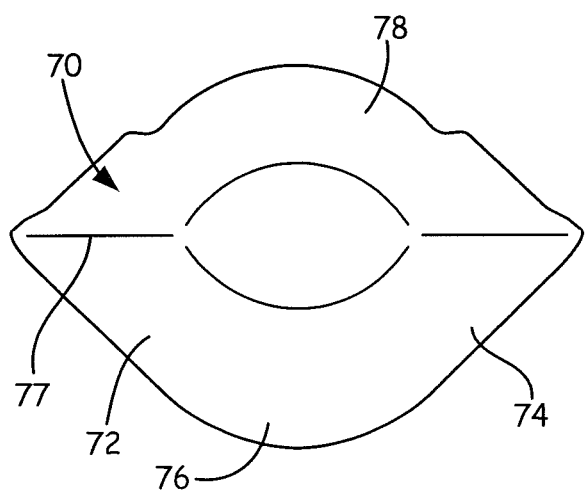
FIG. 8 is a bottom view of the foot and corner protector.

Referring to FIGS. 2, 5 and 7, the foot and corner protector 30 includes a threaded insert 32 having a threaded bore 34 that is molded within a foot portion 36 of the foot and corner protector 30. The threaded bore 34 is aligned with a through bore (not shown) in the bottom surface 12 where a bolt (not shown) is inserted and threadably secured thereto to retain the foot and corner protector 30 to the sterilization tray 10.

Figure 6:
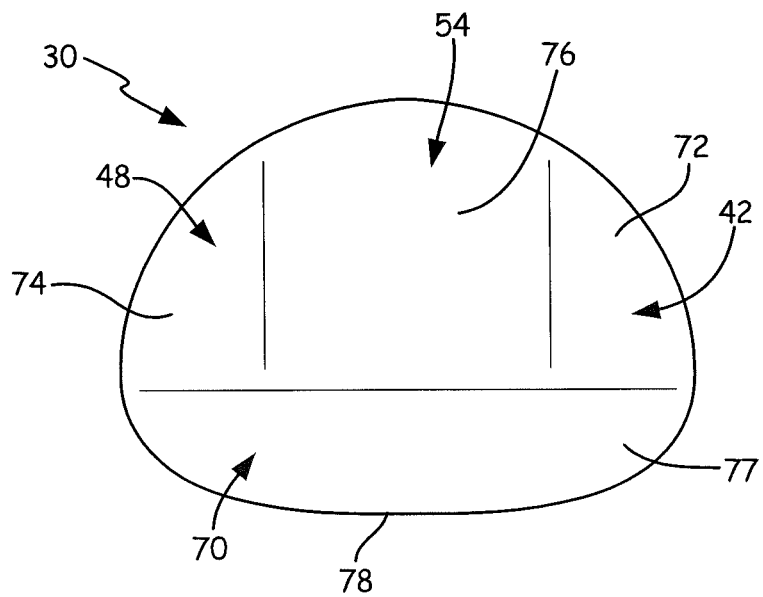
FIG. 6 is a back view of the foot and corner protector.

Referring to FIGS. 5 and 6, it is also contemplated to include a through bore 37 in the foot portion 36 wherein the through bore 33 is configured to accept a securing mechanism, such as but not limited to a bolt or screw. While illustrated as being located in the foot portion 36, one or more through bores 33 can also be located in the foot portion 36, the first side wall portion 42 or the second side wall portion 48.

The foot portion 36 is generally horizontal and includes cut out portion 38 defined by a shoulder 37 and a bottom surface 39. The cut out portion 38 is configured to accept a portion of a foot that is attached to the tray 10. The foot portion 36 is substantially horizontal and by accepting the foot of the tray within the cut out portion 38, the foot portion 36 is configured to engage the sterilize wrap and prevents tearing of the sterile wrap. While the cut out portion 38 is illustrated to accept a foot of a particular tray, such as one marketed under the INSTRU-SAFE® trademark, the cut out portion 38 can be configured to accept any foot of any instrument sterilization tray.

It is also contemplated that the cut out portion 38 may be optionally not required if the sterilization tray does not have a foot. In this embodiment, the foot portion 36 would have a flat bottom surface without a cutout portion 38.

Extending upwardly from a first edge portion 38 of the foot portion 36 is a first side wall portion 42 where the first side wall portion 42 includes an arcuate upper edge 44. The first side wall portion 42 includes a substantially flat inner surface 46 that is configured to be positioned adjacent to one of the side walls 18, 20, 22 and (not shown) of the box portion 11.

A second side wall portion 48 extends upwardly from a second edge portion 40 of the foot portion 36 where the second side wall portion 48 also includes an arced outer edge 50 and a substantially flat inner surface 47 that is also configured to be positioned proximate or adjacent the outer surface of one of the side wall 18, 20, 22 and (not shown) of the box portion 11.

An intermediate corner portion 54 extends from an intermediate edge portion 60 located between the first and second edge portions 38 and 40. The intermediate corner portion 60 connects the first and second side wall portions 40 and 48 together to form a continuous inner surface that conforms to a particular sterilization tray 10. As illustrated, the sterilization tray 10 has a gap between the walls 18, 20, 22, 24 and therefore to insure a snug fit, the intermediate portion 60 of the foot and corner protector 30 includes a convex inner surface 55 configured to be positioned within a gap between two adjacent walls 18, 20, 22, 24.

The interior surfaces of the foot and corner protector 30 is designed to conform to a particular geometry of a sterilization tray 10 by providing complementary inner surfaces are configured to be positioned proximate the three outer surface of the tray 10 that define the corner. It is contemplated that the inner surfaces that define the engaging surfaces of the foot and corner protector 30 can modified to conform to the geometry of any configuration of a corner of a sterilization tray.

The first edge portion 38, the second edge portion 40 and the intermediate edge portion 60 include a concave curve or radius which are configured to accept edges of the joined walls that define the corner of the box portion 11 and the cover 13.

Referring to FIGS. 3, 4, 6 and 8, the outer surface 70 of the foot and corner protector 30 is substantially smooth around the entire outer surface 70 where there are no abrupt edges or transitions. Outer surfaces 72, 74 and 76 of the left and right wall portions 40, 48, the intermediate corner portion 54 have no sharp transitions or edges and gradually transition from one vertical portion 72 of the left side wall portion 42 to the vertical portion 76 of the intermediate corner portion 54 to the vertical portion 74 of the right wall portion 48.

The outer surface 70 includes a convex arced transition or radius 77 on the outer surface 70 from the vertical portions 72, 74 and 76 of the outer surface 70 of the foot and corner protector 30 to an outer surface 78 of the foot portion 36 of the foot and corner protector 30. As there are no sharp edges on any portion of the outer surface 70 of the foot and corner protector 30 and the foot and corner protector 30 increases the radius of the corner of the sterilization instrument tray 10, the foot and corner protector 30 prevents the sterilization wrap from being torn or punctured at the corners of the tray 10.

As illustrated, the foot and corner protector 30 is made of a silicone material that is molded around the insert 32. However, other materials of construction are also contemplated. Further, other removably attachable securing mechanisms besides a threaded engagement are also contemplated.

Because the foot and corner protectors 30 and the corner protector 31 are removably secured to the corners of the box portion 11 and the cover 13, there is no danger of the corner protectors 30 and the corner protectors 13 slipping or otherwise dislodging out of place from the corner of the box portion 11 or the cover 13, which can occur with other corner protectors that are not secured to the tray or the cover. Further, because the foot and corner protectors 30 and the corner protectors 31 are removably secured, once a foot and corner protector 30 or a corner protector 31 requires replacement, an operator can simply reverse the threaded engagement to remove the bolt from the threaded insert 32 and therefore allow the corner protector 30 and/or the corner protector 31 to be easily replaced. As such the present disclosure provides a convenient way of preventing the corners of a sterilization tray 10 from tearing through the sterile wrap while also retaining the corner protectors 30 and 31 in a selected position on the box portion 11 and the cover 31.

Figure 9:
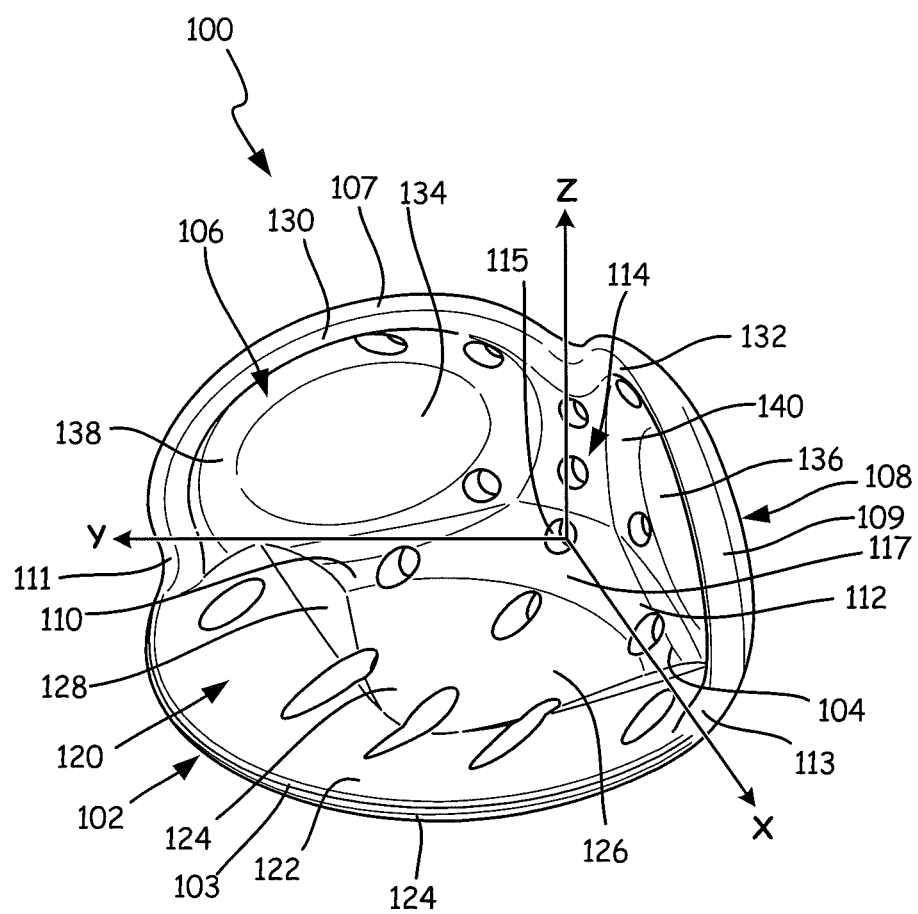
FIG. 9 is perspective view of another foot and corner protector.
Figure 10:
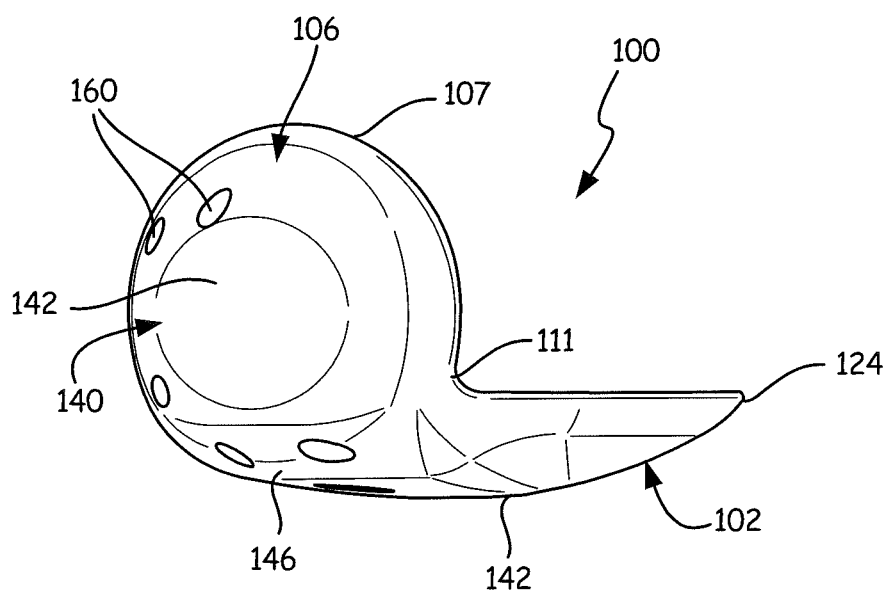
FIG. 10 is a left side view of the foot and corner protector.
Figure 11:
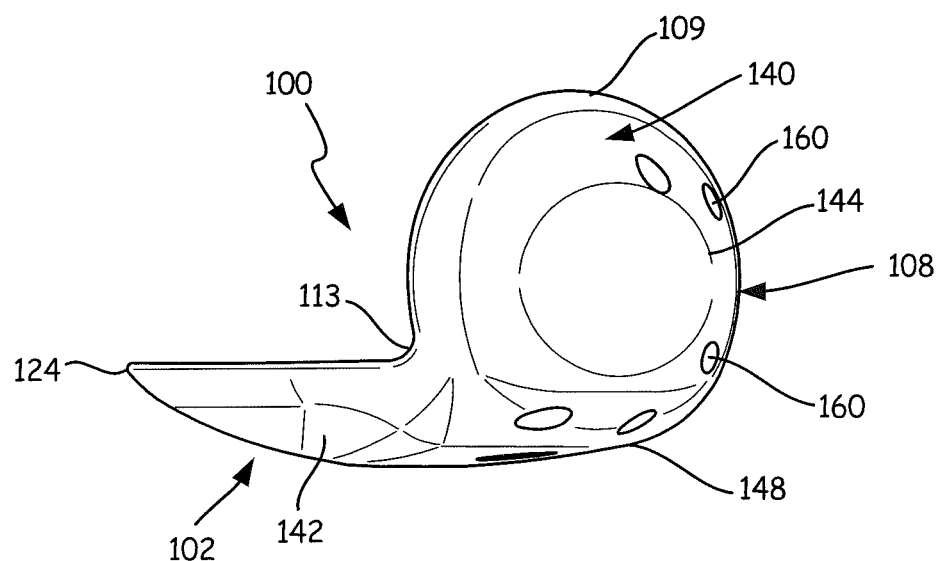
FIG. 11 is a right side view of the foot and corner protector.

Referring to FIG. 9, another corner protector is illustrated at 100. The corner protector 100 is of a monlithic construction and is typically formed through a molding process. A typical material of construction is silicone.

Figure 12:
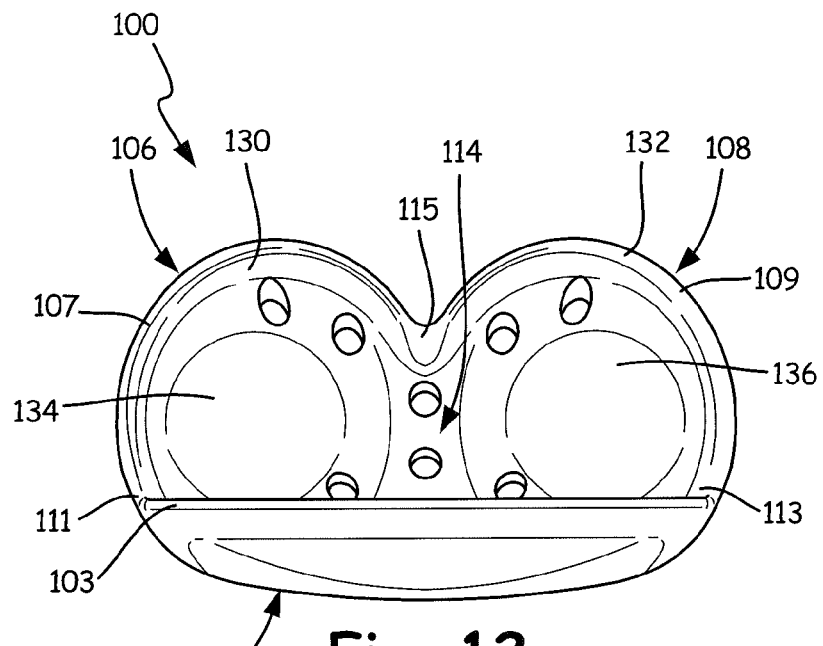
FIG. 12 is a front view of the foot and corner protector.
Figure 13:
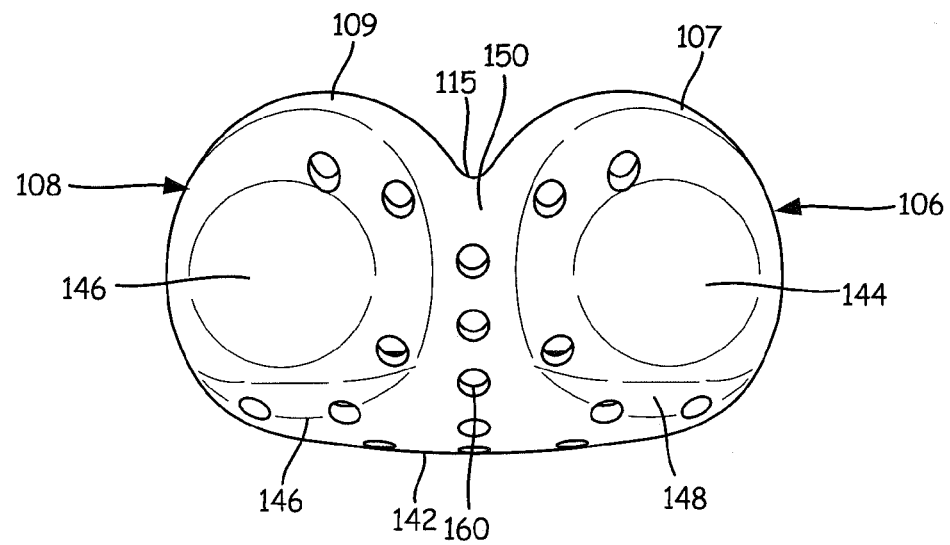
FIG. 13 is a back view of the foot and corner protector.
Figure 14:
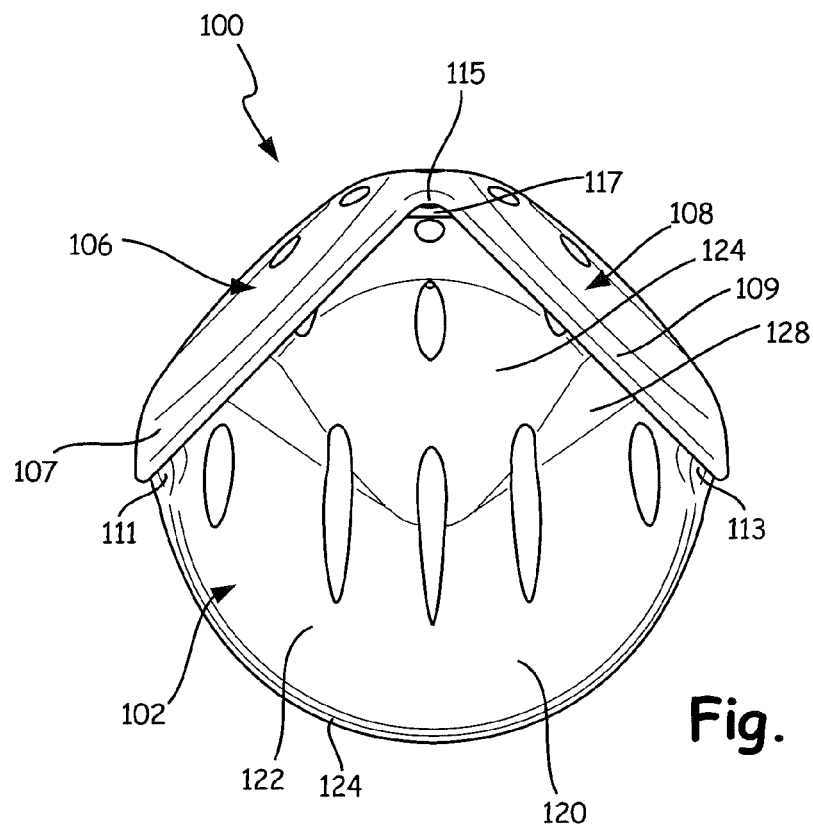
FIG. 14 is a top view of the foot and corner protector.
Figure 15:
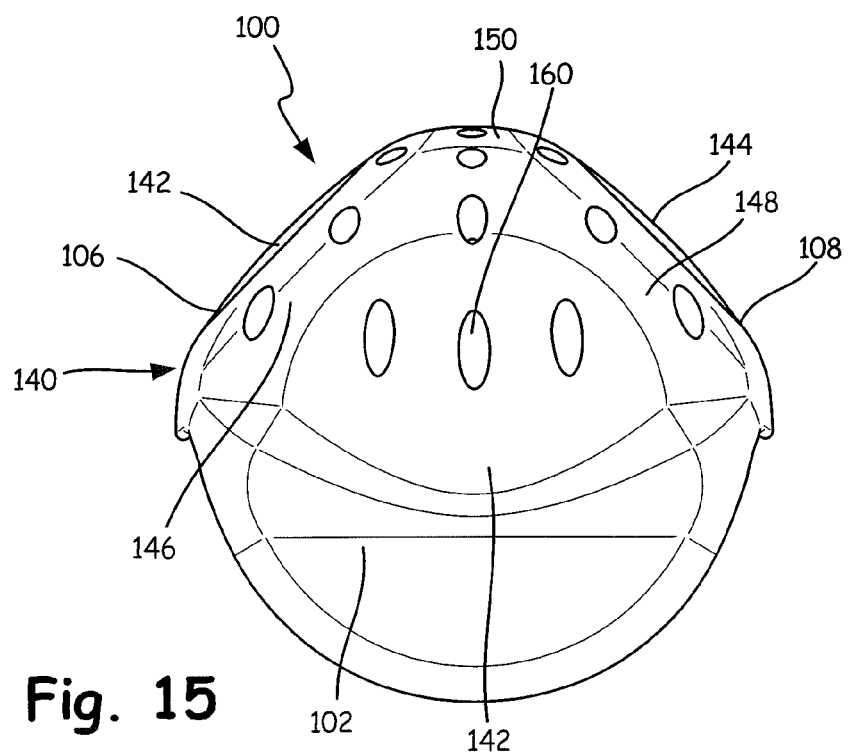
FIG. 15 is a bottom view of the foot and corner protector.

Referring to FIGS. 9, 12 and 14, the corner protector includes a base portion 102 having a perimeter 104 and left and right side wall portions 106 and 108 extending from the perimeter 104 wherein the left and right side wall portions 106 and 108 are substantially orthogonal to each other.

The left and right side wall portions 106 and 108 are connected to the base portion 102 with left and right transition portions 110 and 112, respectively. The left and right side wall portions 106 and 108 are connected with a substantially vertical transition portion 114. Outer surfaces 111, 113, 115 of the transition portions 110, 112 and 114, respectively have concave notches that are configured to accept the three edges of a corner of the equipment sterilization tray and to provide support for retaining the corner protector 100 to the equipment sterilization tray. A corner engaging surface 117 is located in the vertical transition portion 114 at a junction of horizontal lines drawn through the notches 113 and 115 and a vertical line drawn through the notch 117. The junction of the lines is proximate a contact area of a corner of the box portion 11 or the cover 13 with the corner engaging surface 117.

An inner surface 120 of the base portion 102 includes a substantially flat distal surface 122 proximate an outer edge 124. The inner surface 120 includes a concave recess 126 defined by a shoulder 128 extending from an inner edge of the distal surface 122. The left side wall portion 106 and the right side wall portions 108 include edge surface 130 and 132 proximate a perimeter of each wall, respectively. The edge surfaces 130 and 132 have a width and are configured to engage vertical wall of the box portion 11 or the cover 13 of the equipment sterilization tray. Extending from the edge surfaces 130 and 132 are concave recess 134 and 136 defined by shoulders 138 and 140, respectively.

The interior surfaces of the corner protector 100 are configured such that when the corner protector is positioned about a corner defined by edges in the x, y and z axes, the corner protector 100 contacts the box portion 11 or the cover 13 at the notches 111, 113 and 15 engage the edges defining the corner and the corner engaging area 117 contacts the corner. The edge surfaces 130 and 132 contact the vertical walls of the corner and the flat distal portion 122 contacts the horizontal surface of the box portion 11 or the cover 13. The contact areas provide sufficient contact to retain the corner protector 100 on a corner without significant movement about the corner area.

Edges 107 and 109 of the left and right side wall portions 106 and 108, respectively, are arcuate and have lobe shape to provide a sufficient surface to engage the vertical walls of the that define the two surfaces of the corner. The base portion 102 also has an arcuate outer edge 103.

A length of the base portion 102 to the left or right wall 106 and 108 is longer than a height of either the left or right wall portions 106 and 108. A mass of material that defines the distal surface is positioned away from the corner engaging surface 115 such that a center of gravity of the corner protector 100 is located a sufficient distance from both the left and right wall portions 106 and 108. With the center of gravity located the sufficient distance from the left and right wall portions 106 and 108, when the corner protector 100 is positioned on a cover 13, the corner protector 100 is retained on the corner of the cover 13 and does not fall from the cover 13.

The concave recesses 126, 134 and 136 of the base portion 102, the left side wall portion 106 and the right side walls 108, respectively, are configured to extend beyond the surfaces of the three walls defining the corner when the corner protector 100 is positioned about the corner. The concave recesses 126, 134 and 136 create spaces between the base portion 102, the left side wall portion 106 and the right side walls 108, respectively, and a respective wall when the corner protector 100 is positioned about the corner.

Referring to FIGS. 10, 11, 13, and 15, an outer surface 140 of the corner protector 100 is defined by convex outer surfaces of 142, 144 and 146 of the base portion 102, the left side wall portion 106 and the right side wall portion 108, where the convex surfaces 142, 144 and 146 extend proximate the edges 103, 107 and 109 of the base portion 102, the left side wall portion 106 and the right side wall portion 108, all respectively. Convex transition portions 146 and 148 between the bottom portion 102 and the left and right side wall portions 106 and 108, respectfully, define substantially continuous outer surface with no sharp edges or abrupt edges that may cause a puncture or tear in a sterile wrap. A convex transition portion 150 defines a continuous surface between the left and right side wall portions 106 and 108, respectively, such that there are no abrupt or sharp edges between the transition from the left side wall portion 106 to the right side wall portion 108 in the outer surface 140.

The convex transitions portions for the corner protector depicted in FIGS. 9-15 have a radius ranging from about 1/16" to about 1/4" where the length, height and width of the corner protector is about 1½". More particularly, the radius of the transition portions is about 1/8". The corner protector illustrated in FIGS. 2-8 has similar dimensions and radii.

When the corner protector 100 is positioned on a corner of a box portion 11 or the cover 13, the convex surfaces 142, 144 and 146 opposite the concave recesses 126, 134 and 136 extend beyond the perimeter of the corner protector 100. In the event that contact is made with or a force is placed upon the corner protector 100 it is likely that the first surface to be engaged is one of the convex surfaces 142, 144 and 146 opposite the concave recesses 26, 134 and 136. As contact is made or a force is placed on one or more of the convex surfaces 142, 144 and 146 opposite the concave recesses 126, 134 and 136, the convex portions 142, 144 or 146 are flatted along with the concave recess 126, 134 and/or 136. The flatting of the surfaces absorbs the contact or force and dissipates the force such that a sterile wrap is less likely to be torn or punctured. The space between the concave recess 126, 134 and/or 136 and the respective wall acts similar to a cushion because the space allows for the movement of the portions base portion 102, the left side wall portion 106 and/or the right side wall portion 108 which absorbs and dissipates the forces caused by contact or other forces.

The corner protector 100 includes a plurality of drain holes 160 in the base portion 102, the left side wall portion 106 and the right side wall portion 108 and the transition portions that connect the base portion 102 to the left and right side wall portions 106 and 108, respectively, and the left and right side wall portions 106 and 108. The plurality of drain holes 160 is substantially parallel to each other. The configuration of the drain holes 140 allows the plurality of drain holes 160 to be formed during the molding process and allows the mold to be separated and remove after the material forming the corner protector 100 has cured by displacing a portion of the mold from the cured corner protector 100. When the mold components are separated, the corner protector 100 with the plurality of drain holes 160 is formed without difficulty in removing the molds, which can be an issue when the drain holes are formed substantially perpendicularly through the thickness of the base portion 102 in surfaces that have surfaces in three dimensions. The configuration and location of the plurality of drain holes 160 allows for the drainage of moisture from between the box portion 11 and/or the cover 13 and the corner protector 100 that is deposited through the sterilization process.

Figure 16:
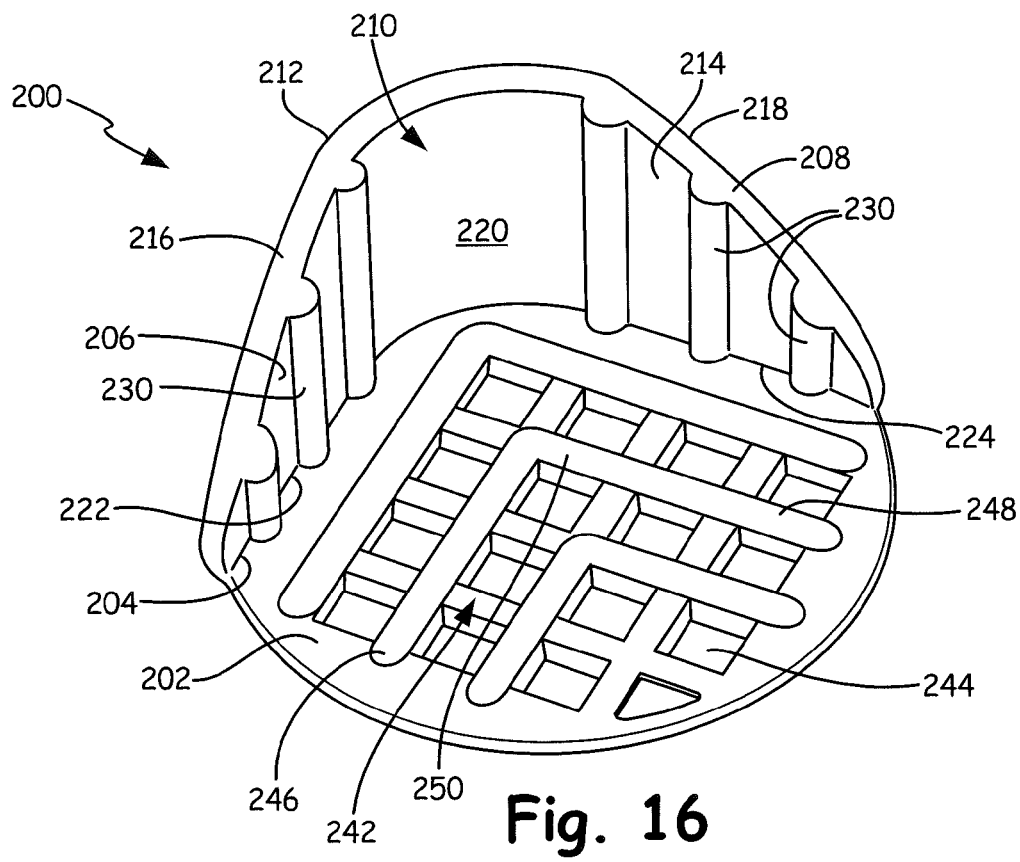
FIG. 16 is a perspective view of another corner protector.

Referring to FIG. 16 another corner protector is illustrated at 200. The corner protector 200 is of a monolithic construction that is formed through a molding process where a typical material of construction is silicone.

The corner protector 200 has a base portion 202 with a perimeter 204. Extending upwardly from the base portion 202 at the perimeter 204 are left and right wall portions 206 and 208. A vertical transition portion 210 connects the left and right wall portions 206 and 208 to form a continuous outer surface 212 and a continuous inner surface 214.

An edge 216 of the left side wall 206 is arcuate and raises in elevation from the corner of the left side wall 206 and the base portion 202 to the vertical transition portion 210. The edge 218 of the right side wall 208 is the mirror image of the edge 216. The edges 210 and 212 form a smooth transition with no abrupt or sudden changes which could cause a puncture or tear in a sterile wrap.

An inner surface 220 of the vertical transition portion 210 is concave and is configured to accept an edge proximate a corner of an equipment sterilization tray. Transitions portions 222 and 224 along the perimeter 204 at the junction of the base portion 202 and the left and right wall portions 206 and 208 are configured to accept edges of edges proximate the corner such that the base portion is positionable on a substantially horizontal surface and the left and right wall portions 206 and 208 are configured to engage vertical side walls on the equipment sterilization tray.

The inner surfaces of the left and right side wall portions 206 and 208 include a plurality of parallel vertical ribs 230. The plurality of ribs 230 are configured to engage vertical walls of the equipment sterilization tray 10 and minimize the contact between the side wall portions 206 and 208 and a wall of the equipment sterilization tray 10 to decrease the time required for the moisture to be removed therebetween.

The base portion 202 includes a grid 242 with ribs defining drain holes 244. The drain holes 244 are configured to allow moisture to pass therethrough. Perpendicular ribs 246 and 248 are raised in the grid 242 to form a raised "V" shaped surface 250 configured to engage the horizontal surface of the equipment sterilization tray 10. As illustrated the corner protector 200 includes three concentric raised "V" shaped surfaces 250. However, the number of raised surfaces 250 can be more or less than three depending upon the desired application. The raised surfaces 250 minimize contact between the base portion 202 and the horizontal surface and thereby decrease the drying time required during the sterilization process.

Figure 17:
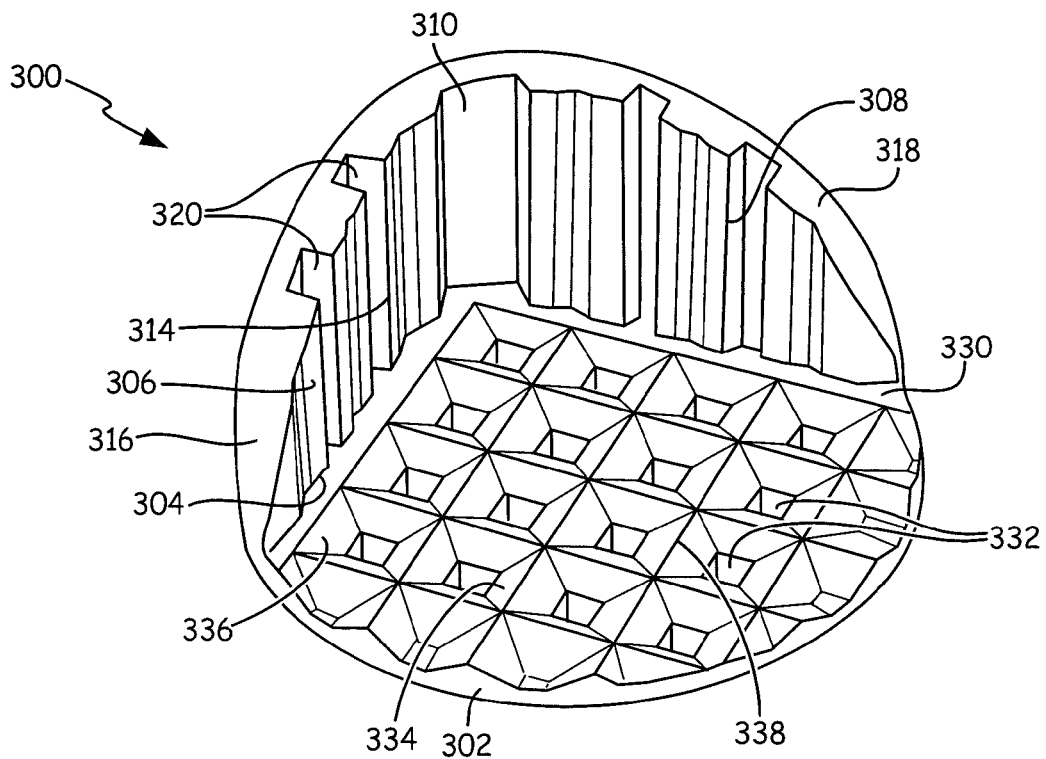
FIG. 17 is a perspective view of another corner protector.

Referring to FIG. 17, another corner protector is illustrated at 300. The corner protector 300 is of a monolithic construction that is formed through a molding process where a typical material of construction is silicone.

The corner protector 300 has a similarly configured outer surface as the corner 200 where the outer surface has smooth transitions and no sharp or abrupt edges.

The corner protector 300 has a base portion 302 with a perimeter 304. Extending upwardly from the base portion 302 at the perimeter 304 are left and right wall portions 306 and 308. A vertical transition portion 310 connects the left and right wall portions 306 and 308 to form a continuous outer surface 312 and a continuous inner surface 314.

An edge 316 of the left side wall portion 306 is arcuate and raises in elevation from the corner of the left side wall 306 and the base portion 302 to the vertical transition portion 310. The edge 318 of the right side wall portion 308 is the mirror image of the edge 316. The edges 310 and 312 form a smooth transition with no abrupt or sudden changes which could cause a puncture or tear in a sterile wrap.

The left wall portion 306 and the right wall portion 308 include a plurality of channels 320 that extend form the base portion 302 to the edges 316 and 318, respectfully. The plurality of channels 320 provide for drainage from between the left and right side wall portions 306 and 308 and the wall of the tray 10 that the side wall portion 306 and 308 contact.

The base portion 302 has a substantially flat top surface 330. The flat surface is interrupted with a plurality of drain holes 332 that are configured in a grid pattern. The drain holes 332 include beveled side walls 334 that form a top portion 336 of each drain hole 332. A top surface of a bevel 334 is adjacent a top surface 334 of a bevel of an adjacent drain hole 332 such that line or thin rib 338 is formed. The line or thin ribs 336 minimize the contact with the surface of the tray and reduces the time required to remove the moisture between the sterilization tray 10 and the corner protector 300.

Although the present invention has been described with reference to preferred embodiments, workers skilled in the art will recognize that changes may be made in form and detail without departing from the spirit and scope of the invention.

The invention claimed is:

1. A corner protector for position about a corner of an equipment sterilization tray, the corner protector comprising:
   a base portion having a perimeter;
   a first wall portion extending from a first portion of the perimeter of the base portion;
   a second wall portion extending from a second portion of the perimeter of the base portion wherein the first and second wall portions are substantially perpendicular to each other;
   a connecting portion extending from a third portion of the perimeter wherein the connecting portion connects the first and second wall portions to form a continuous wall; and
   an insert positioned within the base portion, the insert comprising a surface defining a threaded bore.

2. The corner protector of claim 1 and wherein the first and second wall portion each comprise an arcuate outer edge wherein a distance from the bottom portion to the outer edge gradually increases to a maximum height proximate the connecting portion.

3. The corner protector of claim 1 and wherein the connecting portion comprises a convex inner surface, wherein the convex inner surface extends from proximate the base portion to an outer edge.

4. The corner protector of claim 1 and further comprising a continuous outer wall, the continuous outer wall comprising:
   a substantially flat outer surface of the base portion;
   a substantially flat outer surface of the first wall portion; and
   a substantially flat outer surface of the second wall portion wherein a first transition between the substantially flat outer surface of the base portion and the substantially flat outer surface of the first wall portion is convex and wherein a second transition between the substantially flat base portion and the substantially flat outer surface of the second wall portion is convex and wherein a third transition between the substantially flat surface of the first wall portion and the substantially flat outer surface of the second wall portion is convex such that the outer surface gradually transitions from one surface other without any sharp edges.

5. A corner protector for position about a corner of an equipment sterilization tray, the corner protector comprising:
   a base portion having a perimeter and a first concave recess;
   a first wall portion extending from a first portion of the perimeter of the base portion and comprising a second concave recess;
   a second wall portion extending from a second portion of the perimeter and comprising a third concave recess wherein the first and second wall portions are substantially perpendicular to each other;
   a connecting portion extending from a third portion of the perimeter wherein the connecting portion connects the first and second wall portions to form a continuous wall; and
   a substantially continuous outer surface with no abrupt edges, the substantially continuous outer surface interrupted by at least one through bore.

6. A corner protector for position about a corner of an equipment sterilization tray, the corner protector comprising:

a base portion having a perimeter and a first concave recess;
a first wall portion extending from a first portion of the perimeter of the base portion and comprising a second concave recess;
a second wall portion extending from a second portion of the perimeter and comprising a third concave recess wherein the first and second wall portions are substantially perpendicular to each other; and
a connecting portion extending from a third portion of the perimeter wherein the connecting portion connects the first and second wall portions to form a continuous wall and;
wherein the corner protector comprises a continuous edge surface, the continuous edge surface comprising:
a first arcuate edge portion having a first end and a second end, the first arcuate edge portion defining an edge of the base portion;
a second arcuate edge portion defining an edge of the left side wall portion; the second arcuate edge portion having a first end joining the first end of the first arcuate edge at a first juncture;
a third arcuate edge portion defining an edge of the right side wall portion; the second arcuate edge portion having a first end joining the second end of the first arcuate edge at a second juncture and the second edge of the third arcuate edge portion joining the second end of the second arcuate edge portion at a third juncture.

7. The corner protector of claim 6 and wherein the first, second and third junctures each comprise a notch wherein each notch is configured to accept an edge defining a corner of the equipment sterilization tray.

8. The corner protector of claim 7 and further comprising a corner engaging surface located proximate a juncture of the base portion, the first wall portion and the second wall portion, wherein the corner engaging surface aligns with axes defined by the first notch, the second notch and the third notch.

9. The corner protector of claim 6 and wherein the base portion comprises a length and mass relative to the first and second side wall portions to cause the center of gravity to be located in a selected location in the base portion and a distance from the first and second walls such that the corner protector is configured to be retained on a horizontal surface when placed thereon.

10. The corner protector of claim 9 and wherein base portion includes a distal portion extending beyond the first concave recess which increase the length and mass of the base portion to locate the center of gravity at the selected location in the base portion.

11. The corner protector of claim 5 and wherein the continuous outer surface further comprises:
an outer surface of the base portion;
an outer surface of the first wall portion;
an outer surface of the second wall portion; and
convex transition surfaces between the outer surface of the base portion and the first wall portion, the outer surface and the second wall portion and the first and second wall portions.

12. The corner protector of claim 11 and where the continuous outer surface further comprises:
a first convex portion in the outer surface of the base portion;
a second convex portion in the outer surface of the first wall portion; and
a third convex portion in the outer surface of the first wall portion.

13. The corner protector of claim 5, wherein the at least one through bore is in the base portion.

14. The corner protector of claim 5, wherein the first wall portion and the second wall portion each include the plurality of through bores at least one through bore.

15. The corner protector of claim 14, wherein the at least one through bore comprises a plurality of through bores which are substantially parallel to each other.

16. The corner protector of claim 14, wherein the at least one through bore comprises a plurality of through bores which are substantially parallel to the base portion.

17. A corner protector for position about a corner of an equipment sterilization tray, the corner protector comprising:
a base portion having a perimeter and a first concave recess;
a first wall portion extending from a first portion of the perimeter of the base portion and comprising a second concave recess;
a second wall portion extending from a second portion of the perimeter and comprising a third concave recess wherein the first and second wall portions wherein the first and second wall portions are substantially perpendicular to each other;
a connecting portion extending from a third portion of the perimeter wherein the connecting portion connects the first and second wall portions to form a continuous wall; and
a plurality of through bores wherein the plurality of through bores are substantially parallel to each other and wherein the base portion, the first wall portion and the second wall portion include at least one through bore.

18. The corner protector of claim 17 and wherein the corner protector comprises a continuous edge surface, the continuous edge surface comprising:
a first arcuate edge portion having a first end and a second end, the first arcuate edge portion defining an edge of the base portion;
a second arcuate edge portion defining an edge of the left side wall portion; the second arcuate edge portion having a first end joining the first end of the first arcuate edge at a first juncture;
a third arcuate edge portion defining an edge of the right side wall portion; the second arcuate edge portion having a first end joining the second end of the first arcuate edge at a second juncture and the second edge of the third arcuate edge portion joining the second end of the second arcuate edge portion at a third juncture.

19. The corner protector of claim 18 and wherein the first, second and third junctures each comprise a notch wherein each notch is configured to accept an edge defining a corner of the equipment sterilization tray.

20. The corner protector of claim 17 and wherein the corner protect comprises a continuous outer surface comprising:
an outer surface of the base portion;
an outer surface of the first wall portion;
an outer surface of the second wall portion; and
convex transition surfaces between the outer surface of the base portion and the first wall portion, the outer surface and the second wall portion and the first and second wall portions.

21. The corner protector of claim 20 and where the continuous outer surface further comprises:
a first convex portion in the outer surface of the base portion;
a second convex portion in the outer surface of the first wall portion; and
a third convex portion in the outer surface of the first wall portion.

22. The corner protector of claim 17 and wherein the base portion comprises a length and mass relative to the first and second side wall portions to cause the center of gravity to be located in a selected location in the base portion and a distance from the first and second walls such that the corner protector is configured to be retained on a horizontal surface when placed thereon.

23. The corner protector of claim 22 and wherein base portion includes a distal portion extending beyond the first concave recess which increase the length and mass of the base portion to locate the center of gravity at the selected location in the base portion.

\* \* \* \* \*